(12) United States Patent
Matsumoto et al.

(10) Patent No.: US 8,168,669 B2
(45) Date of Patent: May 1, 2012

(54) THERAPEUTIC AGENT FOR INFLAMMATORY BOWEL DISEASE AND TNF-α PRODUCTION INHIBITOR

(75) Inventors: Hideki Matsumoto, Kawasaki (JP); Tomohisa Okutsu, Kawasaki (JP); Tomoko Takeda, Kawasaki (JP); Hideki Suzuki, Kawasaki (JP); Tetsuo Yano, Kawasaki (JP); Masaki Hashimoto, Kawasaki (JP); Miho Ono, Kawasaki (JP); Manabu Suzuki, Chuo-ku (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 12/491,698

(22) Filed: Jun. 25, 2009

(65) Prior Publication Data

US 2010/0076044 A1    Mar. 25, 2010

Related U.S. Application Data

(60) Division of application No. 11/968,343, filed on Jan. 2, 2008, which is a continuation of application No. PCT/JP2006/313236, filed on Jul. 3, 2006.

(30) Foreign Application Priority Data

Jul. 1, 2005    (JP) ................................. 2005-193591

(51) Int. Cl.
*A61K 31/197* (2006.01)
*A61K 31/4172* (2006.01)
*A61K 31/4184* (2006.01)

(52) U.S. Cl. ........ 514/400; 514/419; 514/561; 514/563; 514/564

(58) Field of Classification Search .................. None
See application file for complete search history.

(56) References Cited

U.S. PATENT DOCUMENTS

| | | | |
|---|---|---|---|
| 5,741,807 A | | 4/1998 | Thomas |
| 5,763,485 A | * | 6/1998 | Smith et al. .................... 514/563 |
| 5,972,985 A | | 10/1999 | Thomas et al. |
| 6,136,859 A | | 10/2000 | Henriksen |
| 2004/0077552 A1 | | 4/2004 | Luger |
| 2004/0096478 A1 | | 5/2004 | Whippie et al. |
| 2004/0116527 A1 | | 6/2004 | Smriga et al. |
| 2005/0020656 A1 | | 1/2005 | Horie et al. |
| 2005/0196468 A1 | | 9/2005 | Salako |

FOREIGN PATENT DOCUMENTS

| | | | |
|---|---|---|---|
| EP | 0 689 835 A2 | | 1/1996 |
| EP | 0 689 835 | * | 1/1996 |
| EP | 1 369 114 A1 | | 12/2003 |
| JP | 8-73351 | | 3/1996 |
| JP | 2003-521481 | | 7/2003 |
| JP | 2003-530411 | | 10/2003 |
| JP | 2003-533436 | | 11/2003 |
| JP | 2004-18418 | | 1/2004 |
| WO | WO 98/13041 | | 4/1998 |
| WO | WO 01/30340 A1 | | 5/2001 |
| WO | WO 01/56405 A2 | | 8/2001 |
| WO | WO 02/11725 A1 | | 2/2002 |
| WO | WO 02/064131 A2 | | 8/2002 |
| WO | WO 02/076445 A1 | | 10/2002 |
| WO | WO 03/055481 A1 | | 7/2003 |
| WO | WO 2005/082377 A1 | | 9/2005 |

OTHER PUBLICATIONS

The Merck Manual (1999), 17th edition, pp. 302-307.*
Herraiz et al., Free Radical Research, (Mar. 2004), 38(3), pp. 323-331.*
Oz et al., Journal of Nutritional Biochemistry, (May 2005), 16, pp. 297-304.*
Kim et al., Journal of Nutritional Biochemistry, (2010), 21, pp. 468-475.*
Takayuki Yamamoto,MD, et al., "Impact of Elemental Diet on Mucosal Inflammation in Patients with Active Crohn's Disease: Cytokine Production and Endoscopic and Histological Findings", Inflammatory Bowel Diseases, vol. 11, No. 6, XP-002596907, Jun. 2005, pp. 580-588.
Supplementary European Search Report issued Aug. 26, 2010, in European Patent Application No. 06780740.41216.
Hideki Suzuki, et al., "Metabolic Syndrome", Diagnosis and Treatment, vol. 92, No. 11, 2004, pp. 2119-2121 (with partial English translation).
G. H. Rabbani, et al., "Antiinflammatory effects of L-histidine in experimental colitis due to shigella flexneri infection in rabbits" Immunopathology/Infectious Diseases, FASEB Journal, vol. 15, No. 4, 2001, p. A587.
G. H. Rabbani, et al., "L-histidine improves colitis in experimental shigellosis in rabbit" HIV and Infectious Disease, FASEB Journal, vol. 14, No. 4, 2000, p. A186.
Ekrem Kaya, et al., "L-Glutamine Enemas Attenuate Mucosal Injury in Experimental Colitis", Disease of the Colon and Rectum, vol. 42, No. 9, 1999, pp. 1209-1215. Ayatoshi Ando, et al., "Effects of Elemental Diet (Elental) Amino Acids in a Mouse Model of Chronic Colitis", The Research Committee of Essential Amino Acids (Japan), No. 175, 2006, pp. 45-48 (with partial English translation).
W. W. Roediger, et al., "Methionine derivatives diminish sulphide damage to colonocytes-implications for ulcerative colitis.", GUT, vol. 39, 1996, pp. 77-81.
Brian E. Meyers, et al., "The Effect of Selected Amino Acids on Gelatin-Induced Inflammation in Adult Male Mice", Inflammation, vol. 3, No. 3, 1979, pp. 225-233.
Dong Ok Son, et al., "Histidine inhibits oxidative stress-and TNF-α-induced interleukin-8 secretion in intestinal epithelial cells", FEBS Letters, vol. 579, 2005, pp. 4671-4677.

(Continued)

*Primary Examiner* — Phyllis G. Spivack
(74) *Attorney, Agent, or Firm* — Oblon, Spivak, McClelland, Maier & Neustadt, L.L.P.

(57) ABSTRACT

Disclosed is an agent for use in the treatment or prevention of inflammatory bowel disease. Also disclosed is an agent for inhibiting the production of TNF-α. A therapeutic or prophylactic agent for inflammatory bowel disease comprising at least one amino acid selected from the group consisting of lysine, histidine, phenylalanine, methionine, tryptophan, glutamine, glycine, cysteine, cystine and threonine, the amino acid being administered at a dose of 0.1 to 4000 mg/kg per day; and a TNF-α production inhibitor comprising an amino acid selected from the group consisting of histidine, phenylalanine and tryptophan, the amino acid being administered at a dose of 0.1 to 4000 mg/kg per day.

4 Claims, No Drawings

OTHER PUBLICATIONS

F. Karmeli, et al., "Cysteine and Methionine—A Novel Modality to Ameliorate Tissue Injury in Experimental Colitis", Gastroenterology, vol. 112, No. 4, Apr. 1997, p. A1009.

Isao Tsune, et al., "Dietary Glycine Prevents Chemical-Induced Experimental Colitis in the Rat", Gastroenterology, vol. 125, Sep. 2003, pp. 775-785.

Johnny W. Peterson, et al., "Anti-inflammatory and Antisecretory Potential of Histidine in *Salmonella*-Challenged Mouse Small Intestine", Laboratory Investigation, vol. 78, No. 5, 1998, pp. 523-524.

Steinberg, et al., Biological Psychiatry (1999), 45:313-320.

Bucci, et al., Separation Science and Technology, 39 (16), pp. 3821-3838 (2004).

* cited by examiner

THERAPEUTIC AGENT FOR INFLAMMATORY BOWEL DISEASE AND TNF-α PRODUCTION INHIBITOR

CROSS REFERENCES TO RELATED APPLICATIONS

This application is a divisional of U.S. patent application Ser. No. 11/968,343, filed on Jan. 2, 2008, which is a continuation of International Patent Application No. PCT/JP2006/313236, filed on Jul. 3, 2006, and claims priority to Japanese Patent Application No. 2005-193591, filed on Jul. 1, 2005.

TECHNICAL FIELD

The present invention relates to an agent for treating or preventing an inflammatory bowel disease, comprising a particular amino acid(s). The present invention also relates to an agent for inhibiting TNF production, comprising a particular amino acid(s).

BACKGROUND ART

An inflammatory bowel disease is a generic term for enteropathy with inflammation, and mainly includes ulcerative colitis and Crohn's disease. The ulcerative colitis is a diffuse non-specific inflammatory disease where large bowel mucosa or submucosa is affected and erosion or ulcer is often formed. Clinical symptoms are mucous and bloody stools, abdominal pain, blood stools, watery stools, fever, lack of appetite, malevolence, emesis and the like. As agents for treating the ulcerative colitis, salazosulfapyridine, adrenal cortex steroids, immunosuppressants, 5-aminosalicylic acid (5-ASA) and the like are used, but it can not be said that these agents are enough to treat the ulcerative colitis.

Crohn's disease is an idiopathic chronic enteritis of unknown cause, and exhibits non-specific inflammatory symptoms in intestines from a small intestine to a large intestine. Its lesions are composed of granulomatous lesions with fibrosis and ulcer, and it is likely that the lesions appear in all gastrointestinal area from an oral cavity to an anus. The clinical symptoms of Crohn's disease include abdominal pain, general malaise, diarrhea, melena, occult blood positive, fever, weight loss, anemia, ileus symptom, abdominal tumor, malevolence, emesis and peritonitis symptom. Crohn's disease simultaneously causes various gastrointestinal and parenteral symptoms, e.g., intestinal stenosis, intestinal perforation, abdominal abscess and heavy hemorrhage which are serious conditions, in addition to nutritional disorder, and often requires procedures such as intestinal surgery. In Japan, a high calorie infusion or an enteral nutrition is performed for the purpose of improving the nutritional condition. In the high calorie infusion, a risk of bacterial translocation is increased. Thus, particularly for a long term, the enteral nutrition is performed. In addition, the therapy by an agent has been attempted. In the drug therapy, salazosulfapyridine, metronidazole, adrenal cortex steroids, immunosuppressants, 5-aminosalicylic acid (5-ASA) and the like are administered. Recently, an anti-TNF antibody has begun to be administered clinically. However, it can be said that the administration of these agents is insufficient yet for treating the Crohn's disease.

TNF-α is an inflammatory cytokine produced by macrophages, macrophage lineage cells (Kupper cells), neutrophils, basophils, eosinophils, lymphocytes, NK cells, LAK cells, mast cells, bone marrow cells, fibroblasts, astrocytes, keratinocytes and the like, and has been recently demonstrated to be deeply involved in pathogenesis of many diseases including Crohn's disease. Therefore, it is believed that if the action of TNF-α can be inhibited, it becomes possible to treat those diseases. Currently, steroidal hormone agents and non-steroidal anti-inflammatory agents are applied to some inflammatory diseases. However, they have diverse action points and do not have an inhibitory action specific for TNF-α. Thus, it is likely to elicit harmful side effects. Particularly, the side effect of the steroid agent has become a medical problem. Furthermore, the treatment using an anti-TNF-α antibody and a soluble TNF-α receptor which are peptide macromolecules gives good clinical results in chronic rheumatoid arthritis and Crohn's disease, but sometimes induces serious infectious diseases including tuberculosis and sepsis, and deterioration of demyelinating disease. Occurrence of malignant tumors has been also reported. Additionally, the formation of a neutralization antibody has been reported, and thus they can not be said to be sufficient.

DISCLOSURE OF INVENTION

Problem to be Solved by the Invention

The present invention aims at providing an agent for use in the treatment or prevention of inflammatory bowel diseases. The present invention also aims at providing an agent for inhibiting the production of TNF-α.

Means for Solving Problem

As a result of an extensive study on inflammatory bowel diseases and TNF-α production for accomplishing the above objects, the present inventor has found that an excellent effect is obtained by administering a particular amino acid(s) in a particular amount(s), and completed the present invention.

That is, the present invention provides an agent for treatment or prevention of an inflammatory bowel disease wherein it contains one or more amino acids selected from the group consisting of lysine, histidine, phenylalanine, methionine, tryptophan, glutamine, glycine, cysteine, cystine and threonine, and the amino acids are administered in an amount of 0.1 to 4000 mg/kg per day.

The individual amino acid described herein includes any form of D-type, L-type or a mixture of D and L, and preferably the L-type is used. The individual amino acid may also be in a salt form in addition to the free amino acid. Furthermore, the individual amino acid may be the form of a peptide. In the case of the peptide, the number of the amino acids is preferably 20 or less. A dosage of the amino acid is given in terms of the free amino acid.

The present invention provides an agent for treatment or prevention of an inflammatory bowel disease wherein it contains 0.5 to 2% by weight of tryptophan, 3 to 9% by weight of lysine, 1.5 to 5% by weight of histidine, 4 to 10% by weight of phenylalanine and 9 to 23% by weight of glutamine, and the amino acids are administered in an amount of 0.1 to 4000 mg/kg per day.

Furthermore, the present invention provides an inhibitor of TNF-α production wherein it contains amino acids selected from the group consisting of histidine, phenylalanine and tryptophan, and the amino acids are administered in an amount of 0.1 to 4000 mg/kg per day.

Still further, the present invention provides an inhibitor of TNF-α production wherein it contains 0.5 to 2% by weight of tryptophan, 3 to 9% by weight of lysine, 1.5 to 5% by weight of histidine, 4 to 10% by weight of phenylalanine and 9 to 23% by weight of glutamine, and the amino acids are administered in an amount of 0.1 to 4000 mg/kg per day.

BEST MODES FOR CARRYING OUT THE INVENTION

The inflammatory bowel disease to which the agent for treatment or prevention of the present invention is applied is an intestine-related disease, and the agent is effective for example for ulcerative colitis and Crohn's disease.

The agent for treatment or prevention of the inflammatory bowel disease of the present invention contains the amino acids selected from the group consisting of lysine, histidine, phenylalanine, methionine, tryptophan, glutamine, glycine, cysteine, cystine and threonine. One or more amino acids may be contained. In light of therapeutic or preventive effect, the agent for treatment or prevention of the inflammatory bowel disease of the present invention preferably contains the amino acids selected from the group consisting of lysine, histidine, phenylalanine, tryptophan and glutamine, and most preferably contains tryptophan. One or more amino acids selected from the group consisting of lysine, histidine, phenylalanine, and glutamine may be contained in addition to tryptophan.

The agent for treatment or prevention of inflammatory bowel disease of the present invention is administered in the amount of 0.1 to 4000 mg/kg of the amino acid(s) (when two or more amino acids are contained, the amount is a total thereof) per day. In light of therapeutic or preventive effect, the agent for treatment or prevention of the inflammatory bowel disease of the present invention is preferably administered in the amount of 0.1 to 1000 mg/kg and most preferably 1 to 500 mg/kg of the amino acid(s) per day.

Furthermore, the amino acids other than the above, e.g., isoleucine, leucine, valine, arginine, alanine, aspartic acid, proline, serine, tyrosine, glutamic acid, asparagine and the like may be contained.

In another embodiment, the agent for treatment or prevention of the inflammatory bowel disease of the present invention contains 0.5 to 2% by weight of tryptophan, 3 to 9% by weight of lysine, 1.5 to 5% by weight of histidine, 4 to 10% by weight of phenylalanine, and 9 to 23% by weight of glutamine. In light of therapeutic or preventive effect, the agent for treatment or prevention of the inflammatory bowel disease of the present invention contains 0.9 to 1.5% by weight of tryptophan, 4 to 7.1% by weight of lysine, 2 to 4% by weight of histidine, 5 to 9% by weight of phenylalanine, and 11 to 20% by weight of glutamine, and most preferably contains 1.0 to 1.3% by weight of tryptophan, 4.5 to 6% by weight of lysine, 2.4 to 3.5% by weight of histidine, 6 to 8% by weight of phenylalanine, and 13 to 17% by weight of glutamine.

The agent for treatment or prevention of inflammatory bowel disease is administered in the amount of 0.1 to 4000 mg/kg per day in terms of the total amount of the amino acids. In light of therapeutic or preventive effect, the agent for treatment or prevention of the inflammatory bowel disease is administered in the amount of 0.1 to 1000 mg/kg and most preferably 1 to 500 mg/kg per day in terms of the total amount of the amino acids.

Furthermore, the amino acids other than the above, e.g., isoleucine, leucine, methionine, threonine, valine, arginine, alanine, aspartic acid, glycine, proline, serine, tyrosine, cysteine, cystine, glutamic acid, asparagine and the like may be contained.

The inhibitor of the present invention inhibits the secretion of TNF-α from TNF-α producing cells such as macrophages, macrophage lineage cells (Kupper cells), neutrophils, basophils, eosinophils, lymphocytes, NK cells, LAK cells, mast cells, bone marrow cells, fibroblasts, astrocytes, keratinocytes and the like. Therefore the inhibitor of the present invention is anticipated as being usable as the agent for treatment or prevention of the diseases where the inhibition of TNF-α production is effective, e.g., sepsis, septic shock, endotoxin shock, oligemic shock, post-oligemic reperfusion injury, meningitis, psoriasis, congestive heart failure, fibrosis, hepatitis, insulin independent diabetes, graft rejection, graft versus host disease, cancer, cachexia, arthritis (chronic rheumatoid arthritis, rheumatoid spondylitis, osteoarthritis, other arthritis), inflammatory bone diseases, bone resorption diseases, Behcet's syndrome, infectious diseases (opportunistic infection due to AIDS, cerebral malaria, infection with Mycobacterium), autoimmune diseases (systemic lupus erythematosus, rheumatoid diseases, allergy, multiple sclerosis, autoimmune uveitis, nephrosis syndrome, type I diabetes (IDDM)), Crohn's disease, ulcerative colitis, erythema nodosum, and damage of alveoli due to radiation disorder and hyperoxia.

The inhibitor of the TNF-α production of the present invention contains the amino acids selected from the group consisting of histidine, phenylalanine and tryptophan. One or more of the amino acids may be contained.

The inhibitor of the TNF-α production is administered in the amount of 0.1 to 4000 mg/kg of the amino acid(s) (when two or more amino acids are contained, the amount is the total thereof) per day. In light of inhibitory effect, the inhibitor of the TNF-α production is preferably administered in the amount of 0.1 to 1000 mg/kg and most preferably 1 to 500 mg/kg of the amino acid(s) per day.

Furthermore, the amino acids other than the above, e.g., lysine, methionine, glutamine, glycine, cysteine, cystine, threonine, isoleucine, leucine, valine, arginine, alanine, aspartic acid, proline, serine, tyrosine, asparagine, glutamic acid and the like may be contained.

In another embodiment, the inhibitor of the TNF-α production of the present invention contains 0.5 to 2% by weight of tryptophan, 3 to 9% by weight of lysine, 1.5 to 5% by weight of histidine, 4 to 10% by weight of phenylalanine and 9 to 23% by weight of glutamine. In light of inhibitory effect, the inhibitor of the TNF-α production of the present invention preferably contains 0.9 to 1.5% by weight of tryptophan, 4 to 7.1% by weight of lysine, 2 to 4% by weight of histidine, 5 to 9% by weight of phenylalanine and 11 to 20% by weight of glutamine, and most preferably contains 1.0 to 1.3% by weight of tryptophan, 4.5 to 6% by weight of lysine, 2.4 to 3.5% by weight of histidine, 6 to 8% by weight of phenylalanine and 13 to 17% by weight of glutamine.

The inhibitor of the TNF-α production is administered in the amount of 0.1 to 4000 mg/kg per day in terms of the total amount of the amino acids. In light of inhibitory effect, the inhibitor of the TNF-α production is preferably administered in the amount of 0.1 to 1000 mg/kg and most preferably 1 to 500 mg/kg per day in terms of the total amount of the amino acids.

Furthermore, the amino acids other than the above, e.g., methionine, glycine, cysteine, cystine, threonine, isoleucine, leucine, valine, arginine, alanine, aspartic acid, proline, serine, tyrosine, asparagine, glutamic acid ant the like may be contained.

The agent for treatment or prevention of the inflammatory bowel disease and the inhibitor of the TNF-α production of the present invention may be appropriate formulations, and are prepared in the form of, for example, powders, particles, granules, tablets, capsules and liquids.

As additives added to the powders, particles, granules, tablets and capsules, for example, excipients (e.g., lactose, glucose, D-mannitol, starch, crystalline cellulose, calcium carbonate, kaolin, light silic acid anhydrate, trehalose), binders (e.g., starch glue liquid, gelatin solution, hydroxypropylcellulose, hydroxypropylmethylcellulose, polyvinyl pyrrolidone, ethanol), disintegrants (e.g., starch, gelatin powder, carboxymethylcellulose, carboxymethylcellulose calcium salt), lubricants (e.g., magnesium stearate, talc), coating agents (e.g., hydroxypropylcellulose, hydroxypropylmethylcellulose, acetylcellulose, saccharose, titanium oxide) are available. Additionally if necessary, coloring agents, flavoring agents and odor improving agents are added. As the additives added to oral liquid agents, preservatives (e.g., benzoic acid, paraoxybenzoate ester, sodium dehydroacetate), suspending agents and emulsifiers (e.g., gum arabic, tragacanth, carboxymethylcellulose sodium salt, methylcellulose, egg yolk, surfactant), and sweeteners and acidifiers (e.g., trehalose, citric acid) are available. Additionally, if necessary, coloring agents and stabilizers are added. As solvents used therefor, purified water is mainly used, but ethanol, glycerine and propylene glycol can also be used.

Additionally, nutritional ingredients such as dextrin, protein sources, carbohydrate sources, vitamins, minerals and trace elements may be contained. The protein source may be the protein useful for nutrition supply, and may be any of the animal proteins and plant proteins. As the animal protein, milk proteins are preferable, and particularly low lactose milk proteins and casein are preferable. As the plant protein, a separated soybean protein is preferable. Two or more proteins may be combined. The protein source may be peptides obtained by hydrolyzing the protein. As the carbohydrate source, saccharides are preferable, monosaccharides, disaccharides, and polysaccharides can be included, and more specifically, glucose, fructose, mannose, galactose, sucrose, sugar (may be purified saccharose), maltose, lactose, dextrin, maltodextrin, starch, maize starch, soybean oligosaccharide and sugar alcohol can be included. Two or more of these saccharides may be combined. As the carbohydrate source, it is preferable to contain any one of sugar, dextrin, maltodextrin and maize starch. The vitamins include vitamin B1, vitamin B2, vitamin B6, vitamin B12, vitamin C, vitamin A, vitamin D, vitamin E, vitamin K, vitamin H, folic acid, pantothenic acids and nicotinic acids. Particularly, vitamin C and vitamin E are preferable because they have a property as an antioxidant. The minerals are not particularly limited as long as they are generally used in this field. Specifically, calcium, sodium, potassium, magnesium, chlorine and phosphorus in an inorganic or organic salt form can be included. For each inorganic or organic salt, the same salts as those which have been already placed on the market and combined in the infusion and the enteral nutrition can be used. The trace element is a metal element which is a trace amount but indispensable for a living body. Specifically, zinc, iron, manganese, copper, chromium, molybdenum, selenium, fluorine and iodine in the inorganic and organic salt form are included. Each trace element may be combined in consideration of a daily needed amount.

The agent for treatment or prevention of the inflammatory bowel disease and the inhibitor of the TNF-α production of the present invention can be prepared by standard methods of granulating each active ingredient directly or mixing each active ingredient with the pharmaceutically acceptable additives depending on each formulation and granulating, or dissolving the agent in the appropriate solvent to emulsify or suspend it, and further mixing it with an appropriate base.

The agent for treatment or prevention of the inflammatory bowel disease and the inhibitor of the TNF-α production of the present invention can be administered orally or parenterally. Contents of the above amino acids, additives and nutritional ingredients are controlled so that the aforementioned amount to be administered daily can be accomplished by dosing once or several times daily. The preferable method of administration includes oral administration, enteral administration (trans-gastric administration, trans-duodenal administration, percutaneous endoscopic gastrostomy (PEG) using a tube, or an enema is preferable), and intravenous administration.

EXAMPLES

Therapeutic Effect on Inflammatory Bowel Disease

Balb/c background IL-10 deficient mice were established from C57BL/6 background IL-10 deficient mice by back-crossing for seventh generations. Balb/c background IL-10 deficient mice spontaneously develop the colitis with aging and exhibit symptoms such as diarrhea. Spleen, mesenteric lymph nodes and sacral lymph nodes were collected from the IL-10 gene-deficient Balb/c mice (male) which had developed the colitis detected by observing the diarrhea symptoms. After preparing single cell suspensions, the cells at about $1 \times 10^7$ were injected intraperitoneally to Scid mice which were immunodeficiency mice (hereinafter the Scid mouse injected IP was referred to as an "experiment mouse"). Subsequently, a chow was changed to an experimental diet. As the experimental diet, a standard chow or those obtained by mixing the amino acids with the standard chow shown in the following Tables 1 to 5 were used. At a time point three weeks after cell transfer, the mice were killed, the colon was collected, the intestinal contents were washed out, and its weight was measured. A percentage of inhibiting a weight gain of the colon was calculated by the following formula.

$$\text{Percentage of inhibiting a weight gain of colon} = [1-(\text{Colon weight in target group}-\text{Colon weight in cell transfer group})/(\text{Colon weight in standard chow group}-\text{Colon weight in cell transfer group})] \times 100 (\%)$$

Results are shown in the following Tables 1 to 5. An amino acid mixture A is composed of the following amino acids (% by weight is represented in terms of free amino acid).

L-isoleucine: 4.56% by weight
L-leucine: 6.38% by weight
L-lysine hydrochloride: 6.30% by weight
L-methionine: 4.60% by weight
L-phenylalanine: 6.18% by weight
L-threonine: 3.71% by weight
L-tryptophan: 1.07% by weight
L-valine: 4.98% by weight
L-histidine hydrochloride: 3.56% by weight
L-arginine hydrochloride: 7.99% by weight
L-alanine: 6.38% by weight
Magnesium potassium L-aspartate: 7.35% by weight
Sodium aspartate hydrate: 6.15% by weight
L-glutamine: 13.71% by weight
Glycine: 3.58% by weight
L-proline: 4.47% by weight
L-serine: 8.23% by weight and
L-tyrosine: 0.78% by weight

TABLE 1

|  |  | Normal Non-treatment | Control Standard chow | Example 1 Standard chow + Gln (5%) |
|---|---|---|---|---|
| Colon weight | Mean | 248.6 | 612.5 | 530.5 |
|  | SE | 5.2 | 18.2 | 14.6 |
|  | n | 8 | 8 | 8 |
| Rate of inhibiting weight gain of colon (%) |  |  |  | 22.5 |

TABLE 2

|  |  | Normal Non-treatment | Control Standard chow | Example 2 Standard chow + Lys (5%) | Example 3 Standard chow + His (5%) | Example 4 Standard chow + Cys (5%) |
|---|---|---|---|---|---|---|
| Colon weight | Mean | 219.2 | 556.4 | 392.8 | 429.0 | 414.4 |
|  | SE | 8.3 | 69.3 | 30.8 | 41.1 | 27.4 |
|  | n | 7 | 7 | 7 | 7 | 7 |
| Rate of inhibiting weight gain of colon (%) |  |  |  | 48.5 | 37.8 | 42.1 |

TABLE 3

|  |  | Normal non-treatment | Control Standard chow | Example 5 Standard chow + Gly (5%) | Example 6 Standard chow + Trp (5%) | Example 7 Standard chow + Met (5%) | Example 8 Standard chow + Cys (5%) |
|---|---|---|---|---|---|---|---|
| Colon weight | Mean | 210.1 | 573.0 | 437.1 | 236.7 | 307.7 | 375.4 |
|  | SE | 6.3 | 29.0 | 32.0 | 22.9 | 25.3 | 12.8 |
|  | n | 7 | 7 | 7 | 7 | 7 | 7 |
| Rate of inhibiting weight gain of colon (%) |  |  |  | 37.4 | 92.7 | 73.1 | 54.4 |

TABLE 4

|  |  | Normal Non-treatment | Control Standard chow | Example 9 Standard chow + Amino acid mixture A (10%) | Example 10 standard chow + Amino acid mixture A (20%) | Example 11 Standard chow + Amino acid mixture A (30%) | Example 12 Standard chow + Phe (5%) | Example 13 Standard chow + Thr (5%) |
|---|---|---|---|---|---|---|---|---|
| Colon weight | Mean | 219.2 | 556.4 | 488.6 | 455.5 | 383.3 | 392.8 | 468.2 |
|  | SE | 8.3 | 69.3 | 16.2 | 22.6 | 29.2 | 30.8 | 13.2 |
|  | n | 7 | 7 | 7 | 7 | 7 | 7 | 7 |
| Rate of inhibiting weight gain of colon (%) |  |  |  | 23.4 | 32.1 | 51.1 | 48.5 | 28.8 |

TABLE 5

|  |  | Normal Non-treatment | Control Standard chow | Example 14 Standard chow + Trp (2%) | Example 15 Standard chow + Trp (5%) |
|---|---|---|---|---|---|
| Colon weight | Mean | 204.8 | 585.0 | 425.6 | 262.1 |
|  | SE | 6.0 | 19.3 | 29.1 | 12.1 |
|  | n | 7 | 7 | 7 | 7 |
| Rate of inhibiting weight gain of colon (%) |  |  |  | 41.9 | 84.9 |

In the above model, cell infiltration occurs with the colitis. Thus, the degree of the cell infiltration is reflected in the colon weight and the therapeutic effect on the inflammatory bowel disease can be evaluated by the colon weight (see Ikenoue Y. et al., International Immunopharmacology, 5: 993-1006, 2005).

<Inhibitory Effect on TNF-α Production>

Extraction of Total RNA

The experimental diet obtained by mixing the amino acids shown in Table 6 with the standard chow was given to the experiment mice, and after three weeks, the colon was removed. A colon sample was homogenized with 500 μL of Isogen (Nippon Gene). The homogenate mixed with 100 μL, of chloroform was centrifuged at 15,000 rpm at 4° C. and an aqueous layer was collected. An equivalent amount of 2-propanol was added thereto, which was then centrifuged at 15,000 rpm at 4° C. A resulting pellet was washed with 70% (v/v) ethanol, dried in air and dissolved in water treated with DEPC.

Synthesis of cDNA

All reagents used were from Invitrogen. 0.5 μg Of total RNA and 0.5 μg of oligo (dT) were dissolved in 12 μL of DEPC-treated water, heated at 70° C. for 10 minutes, and cooled on ice for one minute. Subsequently, 4 μL of 5×1st strand buffer, 1 μL of 10 mM dNTP mix and 2 μL of 100 mM DTT were added thereto. The mixture was reacted at 42° C. for 5 minutes. 1 μL (200 U) of SuperScriptII was added, and the mixture was reacted at 42° C. for 50 minutes and 70° C. for 15 minutes.

Quantitative RT-PCR Using SYBR Green

A gene expression assay based on PCR was performed using SYBR Green PCR Master Mix (Applied Biosystems) and ABI PRISM 7700 System. SYBR Green PCR Master Mix comprises SYBR Green and heat resistant DNA polymerase, and detects fluorescence generated by specifically binding SYBR Green to a double strand DNA amplified by PCR using ABI PRISM 7700 System. Gene expression amounts of the samples can be compared by comparing the numbers of PCR cycles at which a significant fluorescence signal is detected for the first time. The cDNA corresponding to 10 ng of total RNA was used as a template of the quantitative PCR, and n=2 or more per sample of measurements were performed. A forward primer and a reverse primer at each 7.5 pmol of each gene were added to 7.5 μL of SYBR Green PCR Master Mix (Applied Biosystems), and the total volume was made to be 15 μL with water. The PCR was performed by 40 cycles of the reaction at 95° C. for 10 seconds, 60° C. for 30 seconds and 72° C. for 30 seconds after reacting at 95° C. for 10 minutes. The sequences of the primers used for the quantitative RT-PCR are as follows.

Forward primer: CCACCACGCTCTTCTGTCTA (SEQ ID NO: 1)

Reverse primer: AGGGTCTGGGCCATAGAACT (SEQ ID NO: 2)

An inhibitory rate of TNF-α mRNA expression was calculated from the following formula.

Inhibitory rate of TNF-α mRNA expression=[1−Relative amount of TNF-α mRNA expression in target group−Relative amount of TNF-α mRNA expression in cell transfer group)/(Relative amount of TNF-α mRNA expression in standard chow group−Relative amount of TNF-α mRNA expression in cell transfer group)]×100(%)

Additionally, the amounts of mRNA for Reg3γ and Gro α were also similarly measured. The following PCR primers were used.

Reg3γ forward primer: AACAGAGGTGGAT GGGAGTG (SEQ ID NO: 3)

Reg3γ reverse primer: GGGTACCACAGTG ATTGCCT (SEQ ID NO: 4)

Groα forward primer: GCTGGGATTCACCT CAAGAA (SEQ ID NO: 5)

Groα reverse primer: AAGGGAGCTTCAGG GTCAAG (SEQ ID NO: 6)

TABLE 6

| Amino acid | Inhibitory rate of TNF-α mRNA expression (%) |
|---|---|
| 5% His | 54 |
| 5% Phe | 84 |
| 30% Amino acid mixture | 49 |
| 2% Trp | 33 |
| 5% Trp | 49 |

TABLE 7

| Amino acid | Inhibitory rate of Reg3γ mRNA Expression (%) |
|---|---|
| 5% His | 84 |

TABLE 8

| Amino acid | Inhibitory rate of Groα mRNA Expression (%) |
|---|---|
| 5% His | 70 |

The invention claimed is:

1. A method for treating an inflammatory bowel disease, which consists essentially of administering 0.5 to 2% by weight of tryptophan, 3 to 9% by weight of lysine, 1.5 to 5% by weight of histidine, 4 to 10% by weight of phenylalanine, and 9 to 23% by weight of glutamine, to a subject in need thereof in an amount of 0.1 to 4000 mg/kg per day.

2. The method of claim 1, wherein said inflammatory bowel disease is Crohn's disease.

3. The method of claim 1, wherein said inflammatory bowel disease is ulcerative colitis.

4. A method for inhibiting TNF-α production, which consists essentially of administering 0.5 to 2% by weight of tryptophan, 3 to 9% by weight of lysine, 1.5 to 5% by weight of histidine, 4 to 10% by weight of phenylalanine, and 9 to 23% by weight of glutamine, to a subject in need thereof in an amount of 0.1 to 4000 mg/kg per day.

* * * * *

SEQUENCE LISTING

<160> NUMBER OF SEQ ID NOS: 6

<210> SEQ ID NO 1
<211> LENGTH: 20
<212> TYPE: DNA
<213> ORGANISM: Artificial
<220> FEATURE:
<223> OTHER INFORMATION: primer

<400> SEQUENCE: 1
ccaccacgct cttctgtcta                                            20

<210> SEQ ID NO 2
<211> LENGTH: 20
<212> TYPE: DNA
<213> ORGANISM: Artificial
<220> FEATURE:
<223> OTHER INFORMATION: primer

<400> SEQUENCE: 2
agggtctggg ccatagaact                                            20

<210> SEQ ID NO 3
<211> LENGTH: 20
<212> TYPE: DNA
<213> ORGANISM: Artificial
<220> FEATURE:
<223> OTHER INFORMATION: primer

<400> SEQUENCE: 3
aacagaggtg gatgggagtg                                            20

<210> SEQ ID NO 4
<211> LENGTH: 20
<212> TYPE: DNA
<213> ORGANISM: Artificial
<220> FEATURE:
<223> OTHER INFORMATION: primer

<400> SEQUENCE: 4
gggtaccaca gtgattgcct                                            20

<210> SEQ ID NO 5
<211> LENGTH: 20
<212> TYPE: DNA
<213> ORGANISM: Artificial
<220> FEATURE:
<223> OTHER INFORMATION: primer

<400> SEQUENCE: 5
gctgggattc acctcaagaa                                            20

<210> SEQ ID NO 6
<211> LENGTH: 20
<212> TYPE: DNA
<213> ORGANISM: Artificial
<220> FEATURE:
<223> OTHER INFORMATION: primer

<400> SEQUENCE: 6
aagggagctt cagggtcaag                                            20